(12) United States Patent
Don Michael et al.

(10) Patent No.: US 7,524,303 B1
(45) Date of Patent: Apr. 28, 2009

(54) ARTERIAL OBSTRUCTION TREATMENT KIT

(75) Inventors: T. Anthony Don Michael, 4109 Sill Pl., Bakersfield, CA (US) 93306; Charles Michael Gibson, Natick, MA (US)

(73) Assignee: T. Anthony Don Michael, Bakersfield, CA (US)

( * ) Notice: Subject to any disclaimer, the term of this patent is extended or adjusted under 35 U.S.C. 154(b) by 654 days.

(21) Appl. No.: 10/870,981

(22) Filed: Jun. 21, 2004

(51) Int. Cl.
*A61M 29/00* (2006.01)
(52) U.S. Cl. ............................. 604/101.01; 604/101.05
(58) Field of Classification Search ............. 604/96.01, 604/101, 264, 101.01, 101.02, 101.03, 101.05; 606/192, 193, 194, 200; 623/1.11
See application file for complete search history.

(56) References Cited

U.S. PATENT DOCUMENTS

| | | | | |
|---|---|---|---|---|
| 4,083,369 A | * | 4/1978 | Sinnreich | 624/103.06 |
| 5,368,579 A | * | 11/1994 | Sandridge | 604/249 |
| 5,833,650 A | * | 11/1998 | Imran | 604/509 |
| 5,895,405 A | * | 4/1999 | Inderbitzen | 606/194 |
| 6,022,336 A | * | 2/2000 | Zadno-Azizi et al. | 604/101.05 |
| 6,203,561 B1 | * | 3/2001 | Ramee et al. | 606/200 |
| 7,169,171 B2 | * | 1/2007 | Don Michael | 623/1.11 |
| 2003/0109916 A1 | * | 6/2003 | Don Michael | 623/1.11 |
| 2003/0120208 A1 | * | 6/2003 | Houser et al. | 604/103.04 |
| 2003/0176909 A1 | * | 9/2003 | Kusleika | 623/1.11 |

* cited by examiner

*Primary Examiner*—Nicholas D Lucchesi
*Assistant Examiner*—Aarti Bhatia
(74) *Attorney, Agent, or Firm*—Browdy and Neimark, P.L.L.C.

(57) ABSTRACT

A kit for performing angioplasty or stenting in a blood vessel, composed of at least two components. One of the components includes a first catheter providing a blood bypass flow path and carrying a blocking balloon and a blood vessel dilation device. Another one of the components includes a second catheter having an imperforate wall enclosing an axial lumen and having an open distal end, a hollow tube surrounding, and movable longitudinally with respect to, the second catheter, and a second blocking balloon carried by the hollow tube.

16 Claims, 2 Drawing Sheets

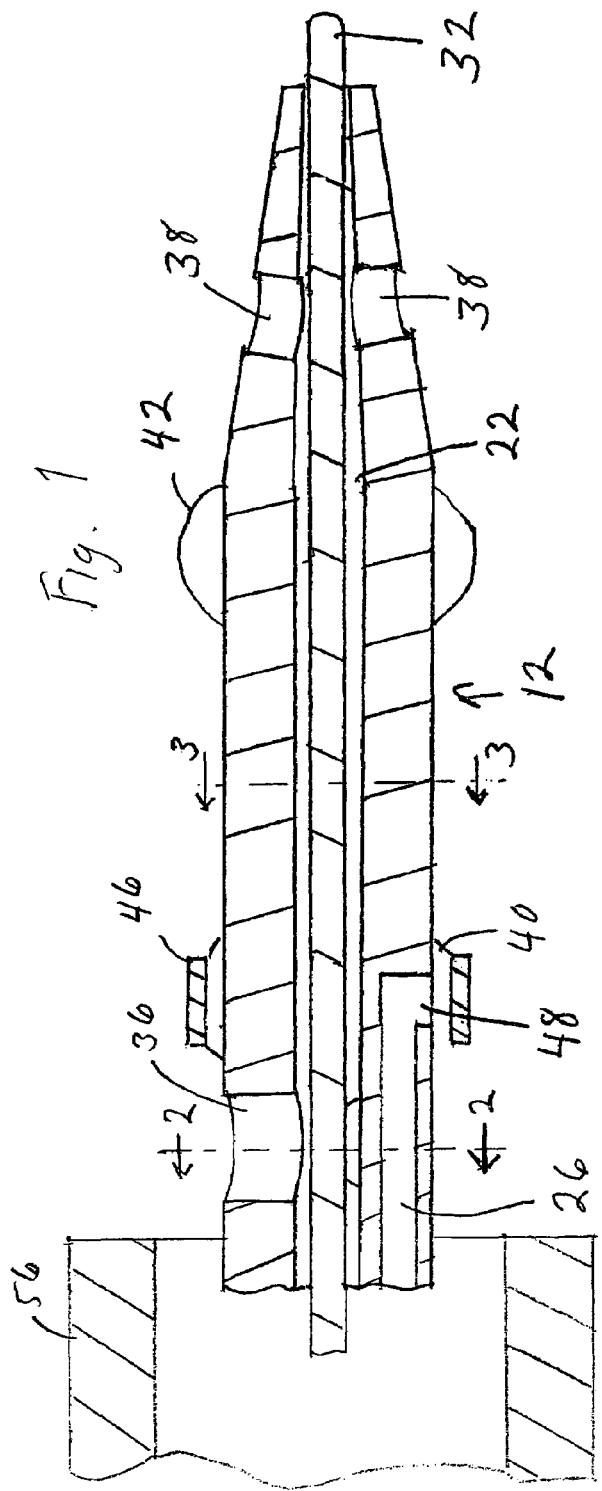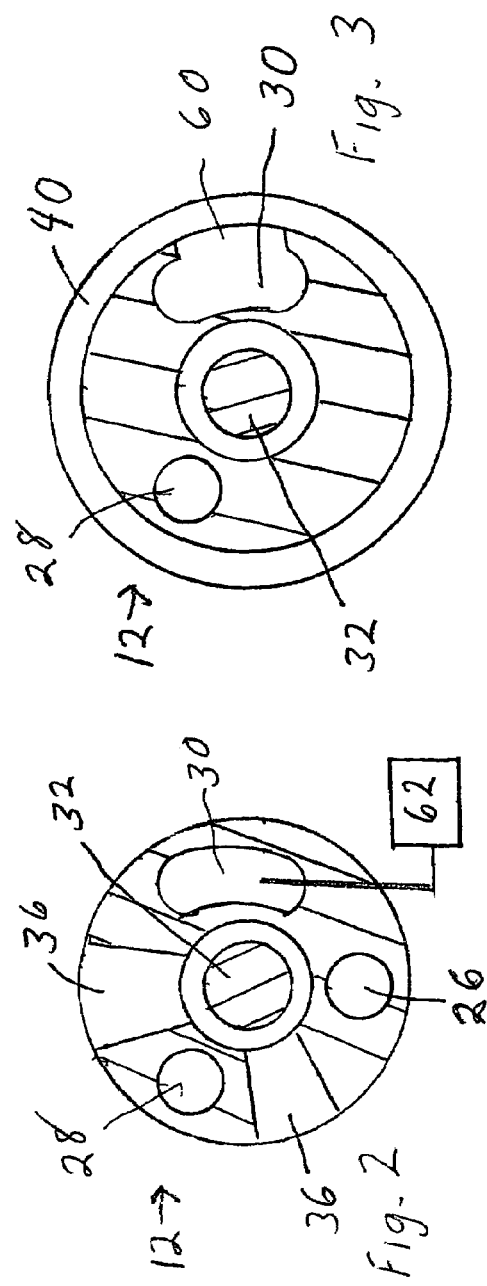

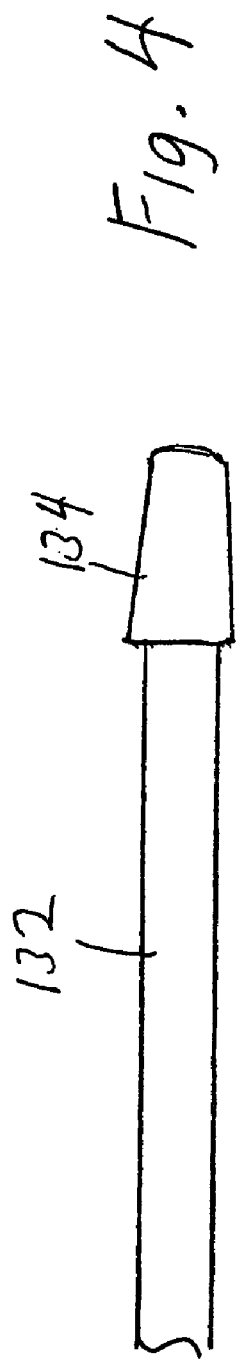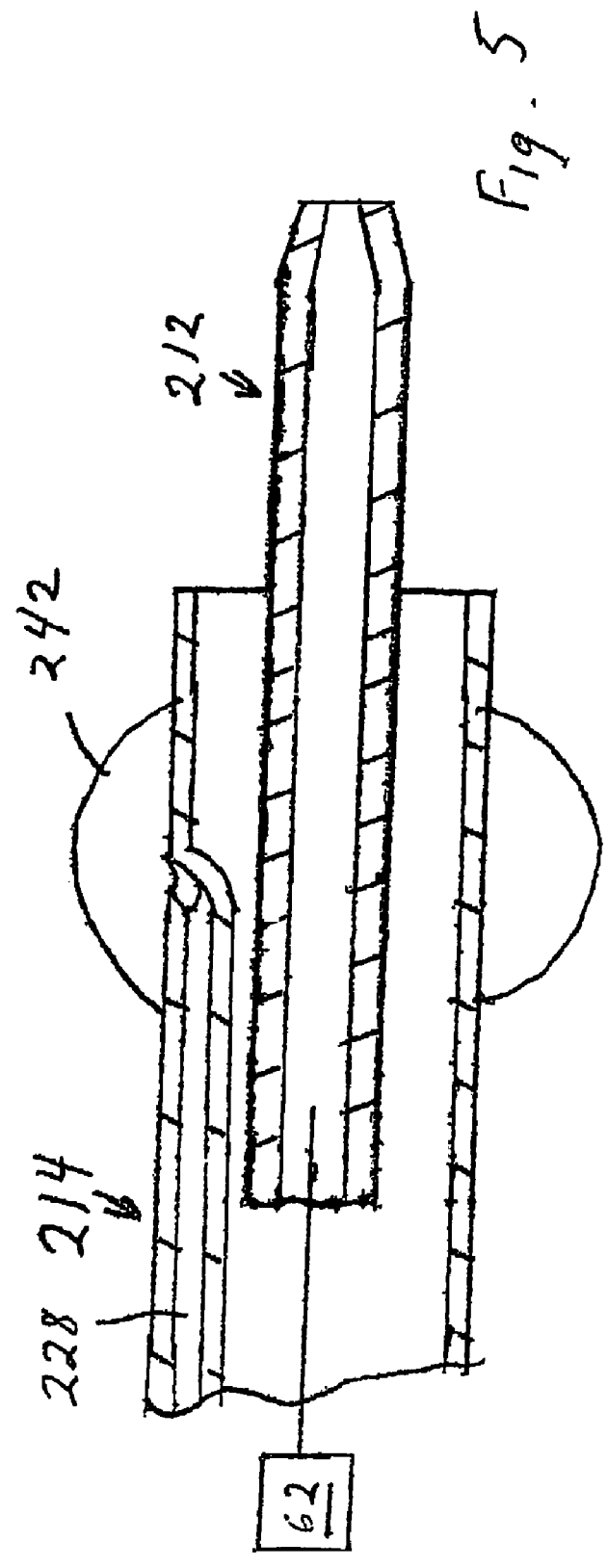

ARTERIAL OBSTRUCTION TREATMENT KIT

BACKGROUND OF THE INVENTION

The present invention relates to the treatment of obstructions in the arteries, and particularly the coronary arteries, and vein grafts of a patient.

There is a growing appreciation for the value of treating arterial obstructions by angioplasty and/or stenting, on an emergency basis. Numerous studies show that emergency angioplasty can save lives if done quickly, and in the current state of the art, this requires an experienced team of doctors, nurses and technicians. It also requires the widespread availability of suitable equipment, which, in the present state of the art, is relatively sophisticated and costly.

BRIEF SUMMARY OF THE INVENTION

The present invention seeks to alleviate these limitations by providing a kit composed of a relatively small number of relatively simple components that are capable of being used in various combinations and/or sequences to successfully treat substantially all arterial obstructions that require urgent treatment.

This is achieved by the provision of a kit for performing an angioplasty, stenting, or clot removal procedure in a blood vessel, and for removing thrombus prior to this procedure, especially in emergency situations. The kit is composed of:

a first component comprising:

a first catheter having a wall enclosing an axial lumen, the first catheter having a distal end and the wall having a substantially circularly cylindrical inner surface and being provided with at least one blood inlet opening spaced from the distal end, at least one blood outlet opening in proximity to the distal end, a fluid delivery and suction opening located between the blood inlet and outlet openings, the blood inlet opening and blood outlet opening communicating with the axial lumen and forming with the axial lumen a blood bypass flow path, and a fluid delivery and suction lumen communicating with the fluid delivery and suction opening;

a first blocking balloon carried by the first catheter at a location between the blood inlet opening and the blood outlet opening; and an expandable blood vessel dilation device carried by the first catheter at a location between the blood inlet opening and the blocking balloon;

a second component composed of a guide wire having a distal and provided with a blocking structure at or near the distal end; and a third component comprising:

a second catheter having a thin, imperforate wall enclosing an axial lumen, the second catheter having an open distal end;

a hollow tube dimensioned to surround, and to be movable longitudinally with respect to, the second catheter; and a second blocking balloon carried by the hollow tube.

The second component is intended to be used in conjunction with the first component.

The third component will be used in a first step to remove any clot that may be present. The second catheter has an outer diameter that is sufficiently small to allow it to move past even substantial clots.

The first component will then be used to perform angioplasty and/or stenting.

BRIEF DESCRIPTION OF THE DRAWINGS

FIG. 1 is a side elevational, cross-sectional view of a preferred embodiment of the first component of a kit according to the invention.

FIGS. 2 and 3 are cross-sectional views taken along lines 2-2 and 3-3 of FIG. 1.

FIG. 4 is a detail view of an additional element of the first component.

FIG. 5 is a cross-sectional view of a preferred embodiment of the third component of a kit according to the invention.

DETAILED DESCRIPTION OF THE INVENTION

A first component of a kit according to the invention is shown in FIGS. 1-3 and is composed essentially of a dilatation and embolic blocking catheter 12.

Catheter 12 is a hollow body provided along its axis with a blood bypass flow lumen 22. The wall of catheter 12 is formed to contain three lumens: a proximal balloon inflation lumen 26; a distal balloon inflation lumen 28; and a fluid delivery and suction lumen 30. Lumens 26 and 28 can each have a circular cross section, while lumen 30 is preferably elongated, as shown, in the circumferential direction to provide an enlarge flow cross section.

Lumen 22 can, but need not, extend the full length of catheter 12 and has a small diameter opening at the distal end thereof for passage of a guide wire 32 that serves to guide catheter 12 to a desired treatment site. Guide wire 32 may be a hollow tube whose distal end is used as a pressure sensor in communication with a pressure monitoring device connected to the proximal end of guide wire 32.

Preferably, the opening at the distal end of catheter 12 is made only slightly larger in diameter than guide wire 32 to allow more accurate guidance of catheter 12.

Catheter 12 is provided with a plurality of blood flow inlet openings 36 and a plurality of blood flow outlet openings 38, each set of openings 36, 38 being distributed to the extent possible circumferentially around the outer lateral wall of catheter 12. Openings 36 and 38 extend through the lateral wall of catheter 12 into communication with lumen 22.

If lumen 22 does not extend through the full length of catheter 12, the proximal end of lumen 22 must be located at a point upstream of openings 36, while the distal end of lumen 22 must be located downstream of openings 38. A separate guide wire lumen may be provided over the entire length of catheter 12. Such a catheter is disclosed in copending U.S. application Ser. No. 10/118,332, filed by T. Anthony Don Michael on Apr. 9, 2002, the disclosure of which is incorporated herein by reference.

A balloon, or a stent deployment sleeve or sheath, 40 and a balloon 42 are carried on the outer surface of catheter 12 at locations between openings 36 and 38. The blood bypass flow path defined by lumen 22 should extend at least across balloon 42 because that balloon remains inflated for a longer period of time, of the order of several minutes, than does balloon 40, which usually remains inflated for a period of the order of a few seconds.

According to preferred embodiments of the invention, balloon 40 is a low compliance angioplasty balloon, sheath, or sleeve, and balloon 42 is a high compliance blocking balloon. In further accordance with the invention, balloon 40 may carry a stent 46 that is to be expanded and deployed against the inner wall of a body passage to be treated. Balloon or sleeve 40 communicates via an opening 48 in the wall of catheter 12 with inflation lumen 26 and balloon 42 communicates via another opening (not shown) in the wall of catheter 12 with inflation lumen 28.

According to common practice in the field, catheter 12 can also be provided with circular radiopaque bands adjacent to the proximal and distal edges of both balloons to assist in proper positioning of the catheter. In practical embodiments of the invention, catheter 12 can have a size of 3 to 4 Fr (nFr=n/3 mm).

According to another feature of the invention, catheter 12 can taper and have a gradually decreasing wall thickness, as shown, in the region between balloon 42 and the distal end of the catheter. The tapering and gradually decreasing wall thickness will give catheter 12 greater flexibility, and thus an improved ability to negotiate bends and traverse severe obstructions in the blood vessel during insertion.

The second component is a guide wire 132, shown in FIG. 4. Guide wire 132 has, at its distal end, an enlargement 134, which may be spherical or, as shown, frustoconical. Enlargement 134 is dimensioned to substantially completely block the tapered distal end of lumen 22, at a point just upstream of outlet openings 38, while being small enough to slide along lumen 22 in order to allow introduction and positioning of wire 132. Preferably, enlargement 134 is dimensioned to provide a gap between itself and the inner wall of catheter 12 that allows some blood flow through lumen 22 when enlargement 134 is positioned upstream of the tapered distal end of catheter 12.

Catheter 12 is associated with a guiding catheter 56 having an inner diameter larger than the outer diameter of stent 46 prior to deployment. Guiding catheter 56 is given a wall thickness sufficient to prevent the catheter from being compressed by the blood vessel wall.

Treatment lumen 30 communicates with the region surrounding catheter 12 and between balloons 40 and 42 via one or more openings 60 in the wall of catheter 12. Lumen 30 is further in communication with a conventional system 62 that will be located outside of the patient's body and that is equipped to supply a treatment fluid or flushing fluid and/or to apply suction through lumen 30. The treatment fluid may contain medication or genetic agents, such as stem cells, to aid repair of damage that may be caused to the blood vessel wall by the removal of clot and/or an angioplasty or stenting procedure.

A third component of the kit according to the invention is shown in FIG. 5 and is composed of a second catheter 212 and a hollow tube 214. Catheter 212 is constituted by an imperforate thin wall that is not provided with any blood flow inlet or outlet openings. Catheter 212 is open at its distal end to allow passage of a guide wire 32 not provided with a bead. Catheter 212 may have an outer diameter of 1-2 Fr, preferably 1.5 Fr, and a wall thickness of 0.127 mm.

Catheter 212 may be coupled to system 62, described above.

Tube 214 carries a high compliance blocking balloon 242 and is provided with a balloon inflation lumen 228 for supplying inflation fluid to balloon 242. Balloon 242 and lumen 228 may correspond structurally and functionally to balloon 42 and lumen 28 of the component shown in FIGS. 1-3.

In order to perform a treatment procedure using the kit according the invention, a guide wire and guiding catheter 56, shown in FIG. 1, are inserted according to conventional procedures until the distal end of guiding catheter 56 is brought to a location a short distance upstream, with respect to the direction of blood flow, of the obstruction.

Then, if conventional diagnostic procedures indicate the presence of clot, the elements of the third component are introduced over the guide wire and through the guiding catheter 56 to a location just upstream of the obstruction. Balloon 242 is inflated to prevent the flow of clot debris in the upstream direction and to anchor tube 214 in position during the procedure, and suction is performed through catheter 212, by operation of system 62, to remove as much of the clot as possible. During this removal step, catheter 212 may be moved forward and back along the axis of tube 214 to aid the removal operation. Suction may alternate with the delivery of a treatment fluid, such as a suitable medication or genetic agents, such as stem cells, supplied by system 62 and conducted through catheter 212. If clot is not present, this procedure with the third component can be omitted.

Then, the extent of the remaining obstruction is evaluated in a conventional manner, as by injecting a contrast solution into the artery through guiding catheter 56.

Then, an angioplasty and/or stenting procedure will be performed with the component shown in FIGS. 1-3.

According to this procedure, after withdrawal of components 212 and 214, catheter 12 is introduced over guide wire 32 and through guiding catheter 56 to a point at which balloon 42 is downstream of the obstruction and the dilation elements 40 and 46 are in line with the obstruction. Guide wire 32 is withdrawn, at least to a point upstream of openings 36, to enlarge the flow cross section of lumen 22 and balloon 42 is inflated to block blood flow through the blood vessel around catheter 12.

Then, guide wire 132 is introduced into lumen 22 to bring enlargement 134 into the tapered portion of lumen 22, just upstream of openings 38, to block blood flow through lumen 22.

Immediately thereafter, balloon or sheath 40 is expanded in order to dilate the obstruction, if a stent is not used, or to expand stent 46 against the obstruction, and thus dilate the obstruction. Debris released from the obstruction will be prevented from flowing downstream through lumen 22 due to blockage of lumen 22 by enlargement 134.

Then, balloon 40 can be deflated, leaving stent 46 in place, and suction can be applied by system 62 through lumen 30 to withdraw debris. During this operation, the application of suction can alternate with the delivery, also from system 62 and through lumen 30, of a flushing liquid and/or a treatment fluid, such as a gene therapy agent and/or stem cells, that aids the growth of normal tissue in the portion of the blood vessel that was damaged by the angioplasty treatment. Alternatively, or in addition, a treatment fluid can be introduced or suction can be performed through guiding catheter 56.

Finally, balloon 42 is deflated and catheter 12 and guide wire 132 are withdrawn.

Thereafter, catheter 212 and tube 214 of the second component may be reintroduced and balloon 242 inflated to allow delivery of a quantity of contrast solution, through catheter 212 or tube 214, in order to allow observation of the angioplasty or stenting result. Then, balloon 242 would be deflated and catheter 212 and tube 214 withdrawn, followed by withdrawal of guide wire 32 and of the guiding catheter 56. If necessary, catheter 12 would be re-introduced to form a further procedure.

In further accordance with the invention, the first component can be used to apply the treatment fluid to the blood vessel wall, either as an incident to an angioplasty or stenting procedure and/or clot removal procedure, or as an independent operation. For this purpose, catheter 12 may already be at the desired treatment location, which may be the location of a previous angioplasty or stenting procedure, or may be brought to that location. Balloon 42 is, or may already be, expanded to its blocking state. Balloon 40 may be placed in a partially inflated state, by appropriate control of the inflation pressure applied to balloon 40, so as to not apply a dilation force to the blood vessel wall or to the stent. In this state, balloon 40 may impede, but not fully block, blood flow around catheter 12. Guide wire 132 will be inserted into lumen 22 in order for enlargement 134 to block fluid flow through lumen 22. Then treatment fluid is introduced to the treatment location from system 62 through lumen 30 and opening 60. With enlargement 134 in place, the flow of both blood and treatment fluid through lumen 22 will be blocked. After an appropriate treatment time, suction may be applied by system 62 to withdraw any remaining treatment fluid. The steps of introducing treatment fluid and suctioning can be repeated if necessary. Upon completion of this treatment, balloons 40 and 42 are deflated and catheter 12 is withdrawn.

After all treatments have been completed, guiding catheter 56 is withdrawn from the blood vessel.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A kit for performing an angioplasty, stenting, or clot removal procedure in a blood vessel, comprising:
    a first component comprising:
        a first catheter having a wall enclosing an axial lumen, the first catheter having a distal end and the wall having a substantially circularly cylindrical inner surface and being provided with at least one blood inlet opening spaced from the distal end, at least one blood outlet opening in proximity to the distal end, a fluid delivery and suction opening located between the blood inlet and outlet openings, the blood inlet opening and blood outlet opening communicating with the axial lumen and forming with the axial lumen a blood bypass flow path, and a fluid delivery and suction lumen communicating with the fluid delivery and suction opening;
        a first blocking balloon carried by the first catheter at a location between the blood inlet opening and the blood outlet opening; and
        an expandable blood vessel dilation device carried by the first catheter at a location between the blood inlet opening and the blocking balloon; and
    a second component composed of a first guide wire having a distal end and provided with a blocking structure at or near the distal end, said first guide wire being insertable through said axial lumen of said first catheter and said blocking structure being dimensioned to be movable through and along said axial lumen but to substantially impede blood flow through said axial lumen when said blocking structure is positioned between said blood inlet opening and said blood outlet opening; and
    a third component comprising:
        a second catheter having a thin, imperforate wall enclosing an axial lumen, the second catheter having an open distal end;
        a hollow tube dimensioned to surround, and to be movable longitudinally with respect to, the second catheter; and
        a second blocking balloon carried by the hollow tube.

2. The kit of claim 1, wherein said expandable blood vessel dilation device carried by said first catheter comprises a balloon, or a stent deployment sleeve or sheath, and a stent.

3. The kit of claim 1, further comprising a second guide wire constituted by a hollow tube having a proximal end and a distal end, the distal end constituting a pressure sensor serving as an input for a pressure monitoring device connected to the proximal end of said guide wire.

4. The kit of claim 1, wherein at least one of said first and second catheters is a hollow thin-walled body.

5. The kit of claim 1 wherein said first catheter has an outer diameter of 3 to 4 Fr over at least a portion of its length.

6. The kit according to claim 5 wherein the wall thickness of said first catheter varies along the length of said first catheter and has a greater value in a region aligned with said blood vessel dilation device than in a region between said first blocking balloon and the distal end of said first catheter.

7. The kit of claim 1, wherein said second catheter has an outer diameter of 1-2 Fr.

8. The kit of claim 7, wherein said second catheter has an outer diameter of 1.5 Fr and a wall thickness of 0.127 mm.

9. The kit of claim 1 wherein said second blocking balloon is a high compliance blocking balloon.

10. A method for performing a medical treatment at a treatment site in a blood vessel, comprising:
    providing a catheter having a wall enclosing an axial lumen, the catheter having a distal end and the wall being provided with at least one blood inlet opening spaced from the distal end, at least one blood outlet opening in proximity to the distal end, a fluid delivery and suction opening located between the blood inlet and outlet openings, the blood inlet opening and blood outlet opening communicating with the axial lumen and forming with the axial lumen a blood bypass flow path, and a fluid delivery and suction lumen communicating with the fluid delivery and suction opening, the catheter carrying a blocking balloon at a location between the blood inlet opening and the blood outlet opening and an expandable blood vessel dilation device at a location between the blood inlet opening and the blocking balloon;
    inserting the catheter into the blood vessel so that the treatment site is between the balloon and the dilatation device;
    placing the dilation device in a state to permit blood flow past the device and around the catheter;
    providing a guide wire having a distal end and provided with a blocking structure that is dimensioned to be movable through and along said axial lumen but to substantially impede blood flow through said axial lumen when said blocking structure is positioned between said blood inlet opening and said blood outlet opening;
    introducing the guide wire and blocking structure into and through the axial lumen to a position where the blocking structure is located between the blood inlet opening and the blood outlet opening to cause fluid flow through the axial lumen to be impeded by the blocking structure; and
    delivering a treatment fluid to the treatment site through the fluid delivery and suction lumen and the fluid delivery and suction opening.

11. The method of claim 10 further comprising, after said step of delivering a treatment fluid, suctioning fluid from the treatment site through the fluid delivery and suction lumen and the fluid delivery and suction opening.

12. The method of claim 11 further comprising repeating said steps of delivering a treatment fluid and suctioning fluid.

13. The method of claim 10, wherein said fluid delivery and suction opening is located between the blocking balloon and the expandable blood vessel dilation device.

14. The kit of claim 1, wherein said fluid delivery and suction opening is located between the blocking balloon and the expandable blood vessel dilation device.

15. A catheter assembly comprising:

a catheter having a wall enclosing an axial lumen, said catheter having a distal end and said wall having a substantially circularly cylindrical inner surface and being provided with at least one blood inlet opening spaced from said distal end, at least one blood outlet opening located between said blood inlet opening and said distal end, a fluid delivery and suction opening located between the blood inlet and outlet openings, the blood inlet opening and blood outlet opening communicating with the axial lumen and forming with the axial lumen a blood bypass flow path, and a fluid delivery and suction lumen communicating with the fluid delivery and suction opening;

a blocking balloon carried by said catheter at a location between said blood inlet opening and said blood outlet opening; and a guide wire having a distal end and provided with a blocking structure at or near the distal end, said guide wire being insertable through said axial lumen of said catheter and said blocking structure being dimensioned to be movable through and along said axial lumen to a location between said blood inlet opening and said blood outlet opening but to substantially impede blood flow through said axial lumen when said blocking structure is positioned between said blood inlet opening and said blood outlet opening.

16. The catheter assembly of claim 15, further comprising an expandable blood vessel dilation device carried by said catheter at a location between said blood inlet opening and said blocking balloon.

* * * * *